United States Patent [19]

Hsu

[11] Patent Number: 5,041,438

[45] Date of Patent: Aug. 20, 1991

[54] METHOD FOR TREATING RETROVIRAL INFECTIONS WITH BENZODIAZEPINE COMPOUNDS

[75] Inventor: Ming-Chu Hsu, New York, N.Y.

[73] Assignee: Hoffmann-La Roche Inc., Nutley, N.J.

[21] Appl. No.: 428,558

[22] Filed: Oct. 30, 1989

[51] Int. Cl.$^5$ ...................... A01N 43/62; A01K 31/55
[52] U.S. Cl. .................................................. 514/221
[58] Field of Search ......................... 514/221; 548/539

[56] References Cited

U.S. PATENT DOCUMENTS

| | | | |
|---|---|---|---|
| 3,123,529 | 3/1964 | Kariss | 167/58 |
| 3,248,223 | 4/1966 | Bauerufeind | 99/2 |
| 3,398,159 | 8/1968 | Berger et al. | 260/326.5 |
| 3,400,128 | 9/1968 | Berger et al. | 260/256.4 |
| 3,405,122 | 10/1968 | Berger et al. | 260/239.3 |
| 3,407,211 | 10/1968 | Berger et al. | 260/326.3 |

OTHER PUBLICATIONS

Berger et al., CA 59:10092b, 1962.
Yamamoto et al., CA 74:22904c, 1971.

*Primary Examiner*—Stanley J. Friedman
*Assistant Examiner*—Russell Travers
*Attorney, Agent, or Firm*—George M. Gould; William H. Epstein; Bruce A. Pokras

[57] ABSTRACT

A method for treating viral infections in a patient with a benzodiazepine derivative compound and compositions.

6 Claims, 3 Drawing Sheets

METHOD FOR TREATING RETROVIRAL INFECTIONS WITH BENZODIAZEPINE COMPOUNDS

TECHNICAL FIELD

The instant invention comprises treating a patient infected with a retrovirus comprising administering to the patient a benzodiazepine compound and compositions.

BACKGROUND OF THE INVENTION

According to the World Health Organization there are currently 96,000 cases of AIDS reported worldwide. It is estimated that by 1992 the number of cases will have increased to 1.2 million. AIDS and AIDS Related Complex (ARC) are caused by infection with retrovirus designated HIV which includes the subtypes HIV-1 and HIV-2. HIV exerts a profound cytopathic effect on the CD4+ helper/inducer T-cells, devastating the function of the immune system. HIV infection also results in neurological deterioration and ultimately death of the infected individual. The field of viral chemotherapeutics has developed in response to the need for agents effective against retroviruses, particularly HIV. There are many ways in which an agent can exhibit anti-retroviral activity, one of which is through inhibition of viral replication. For example the HIV virus requires at least four viral proteins for replication: Reverse Transcriptase (RT), protease, the transactivator protein TAT, and the REV protein. Anti-retroviral agents such as AZT or ddC are known to be RT inhibitors. Anti-viral agents such as TAT inhibitors would act at a different stage of the viral life cycle. HIV replication in latently infected CD4+ lymphocytes is induced when the cells are stimulated to proliferate by cytokines or mitogens. The viral switch from latency to active replication requires the regulatory gene products TAT and REV. The TAT protein transactivates the HIV-LTR promoter and amplifies viral replication many thousand fold. The TAT responsive sequence is mapped within the LTR sequence. Compounds which have anti-TAT activity will thus arrest HIV at the latent stage of viral infection by preventing replication of the provirus that is integrated into the host cell chromosome. Anti-TAT agents are thus useful for therapeutically treating patients infected with HIV including AIDS and ARC patients or asymptomatic carriers.

SUMMARY OF THE INVENTION

The instant invention is directed to a method for treating a patient infected with a retrovirus, particularly HIV, comprising administering to the patient an anti-virally effective amount of a compound or a composition containing a compound of the formula:

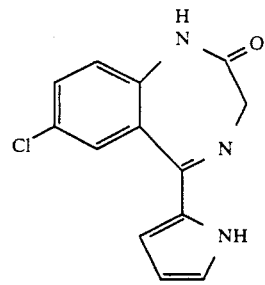

The instant invention is also directed to a method for alleviating the cytopathic destructive effects of retroviral disease in a patient infected with a retrovirus comprising administering to said patient an anti-virally effective amount of Compound I or compositions containing such Compound I.

The instant invention also includes anti-viral compositions comprising a therapeutically effective amount Compound 1 in a pharmaceutically acceptable carrier.

Figure 1:
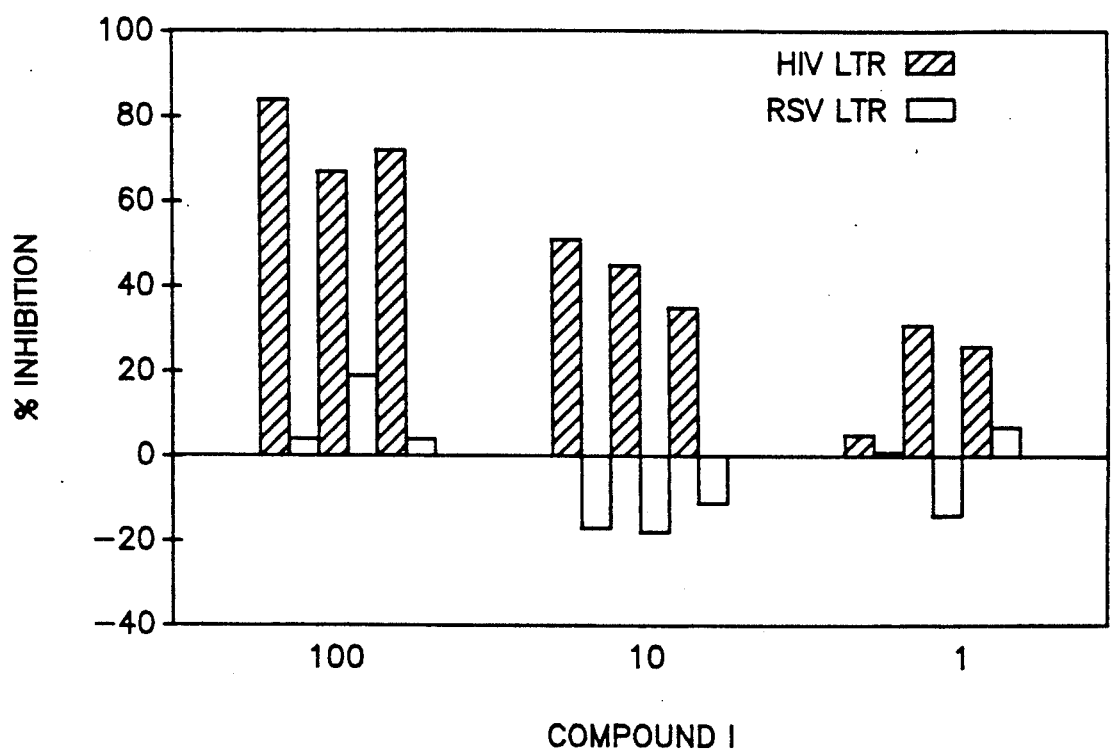
FIG. 1 Illustrates anti-TAT activity of Compound I. COS cells are co-transfected with TAT and Secreted Alkaline Phosphatase (SeAP) genes. The SeAP gene, under the control of the HIV-LTR (responsive to TAT activation) or the RSV-LTR (unresponsive to TAT action) serves as a monitor or reporter gene. SeAP activity in the HIV-LTR combination but not the RSV-LTR combination serves as a measure of TAT activity. Cells containing the RSV-LTR co-transfected gene combination serve as an indicator of the non-specific toxicity of added test compounds. The black bars represent the percent inhibition of SeAP activity by Compound I when the SeAP gene is under the control of HIV-LTR. The hatched bars represent the effect of Compound I on SeAP activity when the SeAP gene is regulated by RSV-LTR. The difference in inhibition of activity of the two SeAP constructs indicates that Compound I specifically inhibits TAT action and does not exhibit nonspecific toxicity. The figure includes results from three separate assays.

The compound which is used in the method of the invention (Compound I) is 7-chloro-5-(2-pyrryl)-3H-1,4-benzodiazepin-2(1H)-one. The synthesis of this compound is disclosed in U.S. Pat. Nos. 3,405,122; 3,398,159; 3,407,211; and 3,400,128 all of which are hereby incorporated by reference. Compound I exhibit anti-retroviral, particularly anti-HIV activity.

Compound I is an anti-viral agent which exhibits anti-TAT activity as set forth in Example 1 and FIGS. I-III. This compound also exhibits anti-HIV activity as demonstrated by its inhibition of HIV-cytopathic effect and viral RNA and antigen production as set forth in Example 2. This compound also exhibits anti-HIV activity as demonstrated by positive results in the p24 viral antigen capture assay as set forth in Example 3. P24 antigen is an internal gag protein component of the virus which is detectable in the circulation of HIV-infected patients during the initial acute infection or in advanced ARC or AIDS. The level of p24 antigen in the circulation is also thought to be a measure of the intensity of HIV replication in an infected patient. It has also been observed that p24 antigen is produced in greater quantity six months immediately preceding onset of severe disease in HIV infected patients. The ability of a compound to decrease levels of circulating p24 antigen is thus a measure of its anti-HIV activity. Known anti-AIDS therapeutics such as AZT and ddC are shown to be active in the p24 assay thus indicating a correlation with activity in the human.

The instant invention is directed to treating patients infected with a retrovirus, comprising administering to the patient an anti-virally effective amount of Compound I or a composition containing Compound I. Patient in the context of the invention means human being and retroviral infection particularly includes HIV infection, including AIDS or ARC patients. An anti-virally effective amount of Compound I for treating a retroviral infection is in the range of 0.1 to 10 mg/kg body weight per day. This dosage may be administered in one or more doses at various intervals such as 2, 4, 6, 8, 12, or 24 hours. The suitable dosage is one that achieves a therapeutic blood level of 0.05–10 $\mu$M, 0.1 to 5 $\mu$M is preferred. This blood level may be best achieved by administering approximately 1–3 mg/kg body weight once or twice per day.

The compounds may be administered in various dosage forms as set forth herein. Either the compounds, compositions, or their pharmaceutically acceptable salts are suitable. Pharmaceutically acceptable salts may be salts of organic acids such as lactic, acidic, malic, or p-toluenesulfonic acid and the like as well as salts of pharmaceutically acceptable mineral acids such as hydrochloric and sulfuric acids and the like.

The compounds are administered in the dosages as set forth herein until alleviation of the retroviral infection. The compounds may also be administered with other anti-retroviral agents and particularly with known reverse transcriptase (RT) inhibitors such as ddC, AZT, ddI, ddA, or other inhibitors which act against other HIV proteins. Treatment with both anti-TAT agents such as Compound I and anti-RT agents should inhibit most or all replicative stages of the viral life cycle. The dosages of ddC and AZT used in AIDS or ARC patients have has been published. A virustatic range of ddC is generally between 0.05 $\mu$M to 1.0 $\mu$M. A range of about 0.005–0.25 mg/kg body weight is virustatic in most patients. The preliminary dose ranges for oral administration are somewhat broader, for example 0.001 to 0.25 mg/kg given in one or more doses at intervals of 2, 4, 6, 8, 12, etc. hours. Currently 0.01 mg/kg body weight ddC given every 8 hours is preferred. When given in combined therapy the anti-RT compound may be given at the same time as Compound I or the dosing may be staggered as desired. The two drugs may also be combined in a composition. Doses of each may be less when used in combination then when they are used as a single agent.

The instant invention is also directed to compositions containing a therapeutically effective amount of Compound I in a pharmaceutically acceptable carrier. It is possible for the Compounds of the invention to be administered alone in solution. However, it is preferred that the active ingredients be administered in a pharmaceutical formulation. In the context of the instant invention formulation means composition. These formulations comprise at least one active ingredient together with one or more pharmaceutically acceptable carriers and/or other therapeutic agents, for example an RT inhibitor. As included within the scope of this invention, "acceptable" is defined as being compatible with other ingredients of the formulation and not injurious to the patient or host cell. These carriers include those well known to practitioners in the art as suitable for oral, rectal, nasal, topical, buccal, sublingual, vaginal, or parenteral (including subcutaneous, intramuscular, intravenous, and intradermal) administration. Compound I may be used in the manufacture of pharmaceuticals for the treatment or prophylaxis of viral infections. The compositions may be conveniently presented in unit dosage form and prepared by methods known in the pharmaceutical art. Such methods include the preparation of the active ingredient in a carrier which may contain additional medicinally active ingredients, for example, Compound I in conjunction with a known RT inhibitor such as ddC or AZT. The compositions of the invention suitable for oral administration may consist of liquid solutions such as an effective amount of the compound dissolved in diluents such as water, saline, or orange juice. Capsules, sachets or tablets, each containing a pre-determined amount of the active ingredient, as a solid or granules; as a solution or suspension in an aqueous liquid; in an oil-in-water emulsion or a water-in-oil liquid emulsion, for example, soft gelatin capsules. Tablet forms may include one or more of lactose, microcrystalline cellulose, colloidal silicon dioxide, croscarmellose sodium, magnesium stearate, stearic acid and other excipients, colorants, and pharmacologically compatible carriers.

Formulations suitable for topical administration include lozenges comprising the active ingredient in a flavor, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations suitable for vaginal administration may be presented as pessaries, tampons, creams, gells, pastes, foams, or spray formulas containing in addition to the active ingredient such carriers as are known in the art to be appropriate.

Formulations suitable for parenteral administration include aqueous and non-aqueous, isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described. In the context of the invention formulation means composition.

The instant invention is also directed to a method for alleviating the cytopathic destructive effects in a patient infected with a retrovirus comprising administering an anti-virally effective amount of the compounds or compositions of the invention. Since Compound I is known to inhibit TAT it can inhibit viral replication at the latent stage. The dosages mentioned previously would be suitable for this purpose. Preferably 1-3 mg/kg body weight given once or twice a day provides the virustatic range of 0.01-5.0 $\mu$M. The compounds can be administered to AIDS patients, ARC patients or asymptomatic HIV-infected patients.

EXAMPLE 1

Compound I was tested for anti-TAT activity in an anti-TAT assay described in copending patent application, now U.S. Ser. No. 07/428,555 filed Oct. 10, 1989, filed on the same day as the instant application and hereby incorporated by reference. At 24 hours post transfection 1, 10, and 100 $\mu$M of test compound was added to the culture media of COS cells transfected with two plasmids, one containing the reporter gene which codes for Secreted Alkaline Phosphatase (SeAP) under control of HIV-LTR, and other containing the TAT gene also under control of HIV-LTR. The alkaline phosphatase activity of the media was assayed 48 hours after addition of test compound. The results are set forth in FIG. 1 which represents three independent assays of the test compound. The anti-TAT activity is measured by the percent inhibition of SeAP gene expression under the control of HIV-LTR. The cytotoxicity of the compound was tested in a parallel assay in which SeAP gene expression is put under control of Rous Sarcoma Virus (RSV)-LTR which does not respond to TAT. The results are set forth in FIG. I which shows that Compounds I is a specific inhibitor of TAT and does not exhibit nonspecific cytotoxicity.

EXAMPLE 2

Testing Compound I for Inhibition of HIV-Cytopathic Effect and Inhibition of Viral RNA and Antigen Production The assay protocols for the inhibition of HIV-cytopathic effect and the reduction of cell-associated viral antigens were modified from published procedures [Mitsuya, et al. P.N.A.S., USA 83:1911 (1986), and Hedenskog, et al., J. Med. Virol. 19:325 (1986)].

High titer virus stocks (HIV-1 NIT strain) were grown in CD4+ CR1O cells in RMPI-1640 media (Gibco Laboratories) supplemented with 10% fetal calf serum and 0.1 mg/ml Gentamicin. The collected media were filtered through a 0.8 Micron filter and virus isolates were concentrated 100 fold and stored at $-80°$ C.

CD4+ CEM cells, propagated in the same medium, were incubated for 60 minutes at 37° C. with diluted stock virus at MOI=1. Cells were washed three times with phosphate buffered saline and resuspended in the medium at $2 \times 10^5$ cells/ml. Various quantities of Compound I were added. Three days after infection, numbers of live cells were counted by trypan blue exclusion [Mitsuya, et al. Proc. Natl. Acad. Sci. 83:1911 (1986)]. At the same time, aliquots of cells were fixed with acetone and stained with antibodies from AIDS patients, followed by a second staining with fluorescein-conjugated goat anti-human IgG (Cappel). Cells stained with the fluorescent antibody were counted using a fluorescence microscope and the results were expressed as percentage of the total number of cells counted [(Hedenskog et al., J. Med. Virol. 1:9325 (1986)].

The viral RNA in infected cells was quantitized with an RNA-RNA hybridization/reversible target capture procedure [Gillespie et al. Molecular and Cellular Probes, 2:73 (1989)]. Reagents were purchased from GeneTrack System (MA, USA) and assays were carried out according to the procedure described by the manufacturers. $2 \times 10^5$ live cells, determined by trypan blue exclusion, were used in each assay.

Figure 2:
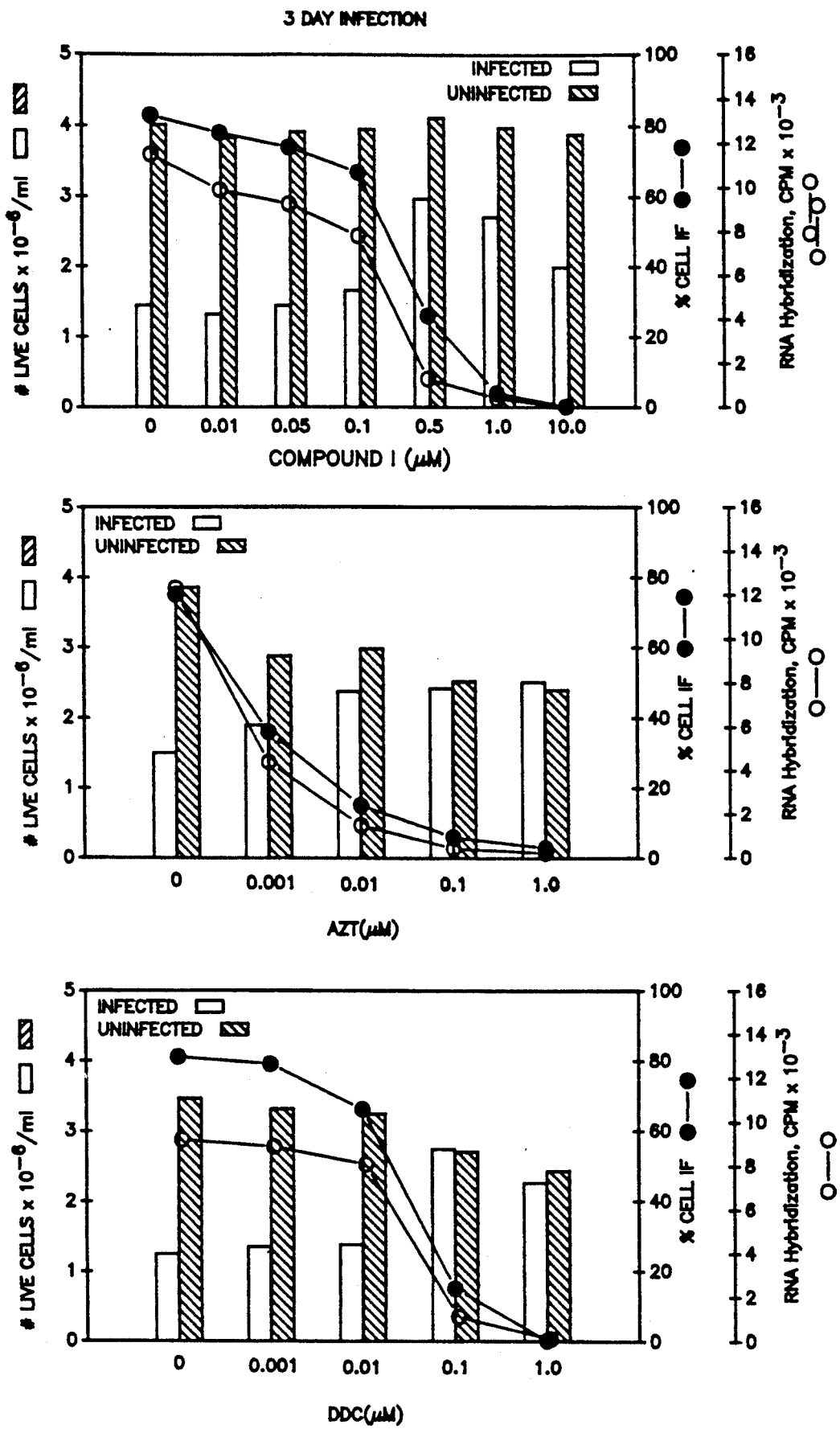
FIG. 2 Illustrates the anti-HIV activity of Compound I when tested according to the protocol set forth in Example 2. The open bars and the hatched bars are live-cell counts of infected and uninfected cells respectively. The full circles are percentage of cells which were stained with antibody from AIDS patients. The open circles represent quantities of viral RNA in infected cells. The duration of treatment for Compound I was 3 days.
Figure 3:
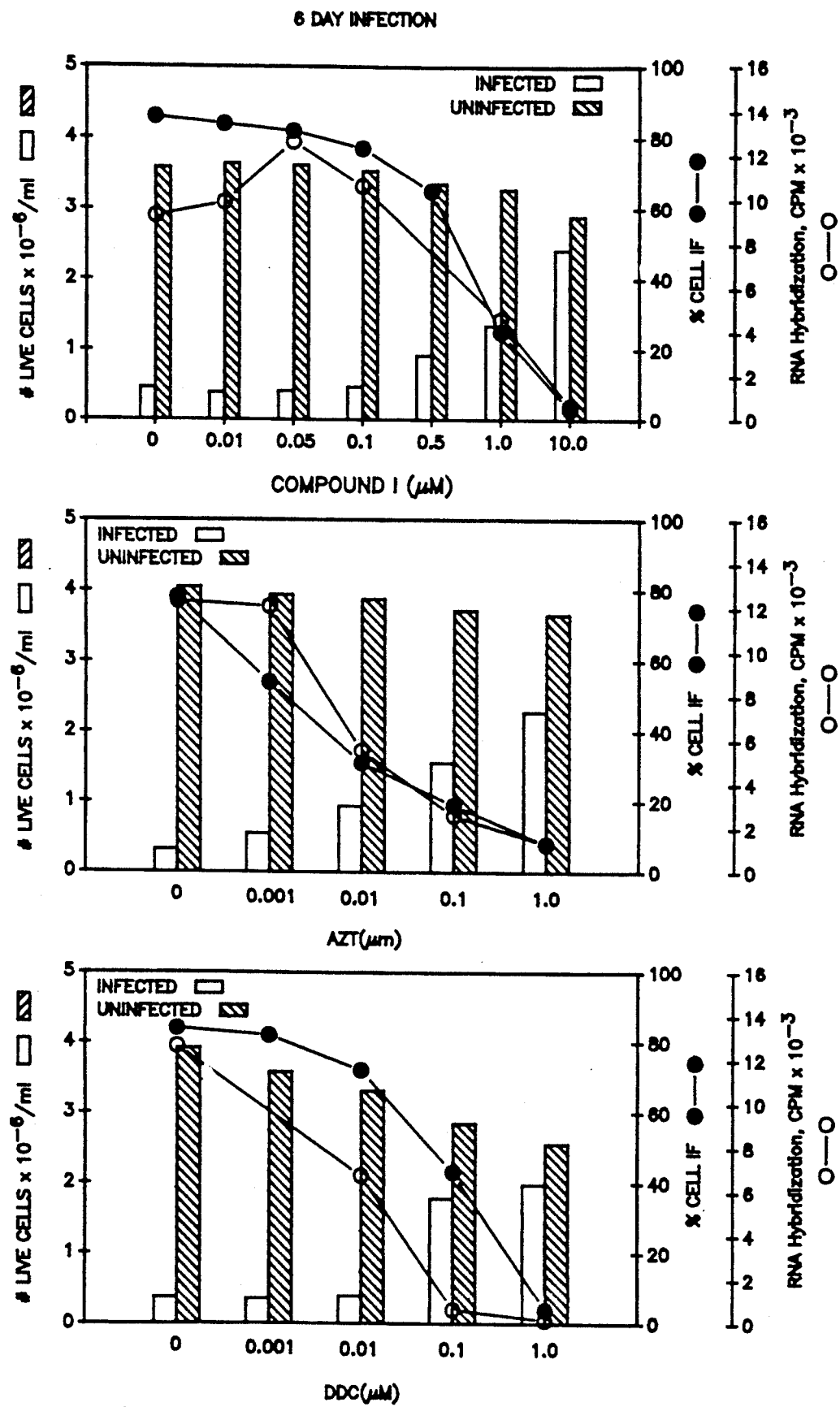
FIG. 3 See legend for FIG. II except the duration of treatment for Compound I was 6 days.

For cytotoxicity testing, uninfected CEM cells were treated with Compound I at similar concentrations and toxicity of the compound was measured by the live-cell count. Two compounds, AZT and DDC, with known potency for the treatment of AIDS, were tested in parallel with Compound I. To test the effect of a longer-term treatment with Compound I, the compound-treated cells above were replated at day 3 in media containing the compound and the assay repeated at day 6. Results of the assays are shown in FIGS. 2 and 3.

EXAMPLE 3

Testing of Compound I for anti-viral activity

Compound I was tested for anti-viral activity in the p24 viral antigen capture assay.

The Enzyme Linked Immuno-absorbant Assay (ELISA) was used to test Compound I for anti-HIV activity by measuring virus replication in CD4+ T-lymphocytes by detecting viral p24 antigen released into the tissue culture supernatant of infected cells.

High titer virus stocks [HIV/HTLV III, RF strain] were grown in H9 cells in RPMI-1640 (Flow Laboratories) supplemented with 10% fetal calf serum, penicillin (100 IU/ml) and streptomycin (100 $\mu$g/ml). Cell debris was removed by low speed centrifugation and the supernatant stored at $-70°$ C. until required. The host cell line used in the anti-viral assays was the C8166 CD4+ T-cell line which is particularly susceptible to infection with HIV. Cells were incubated with 10 TCID$_{50}$, HIV/HTLV III (RF) at 37° C. for 90 minutes and then washed three times with PBS. Cell aliquots ($2 \times 10^5$) were resuspended in 1.5 ml growth medium in 6 ml tubes and appropriate amounts of Compound I added and incubated at 37° C. At 72 hours post-infection, the supernatants from the cell cultures were assayed for p24 antigen. The antigen capture ELISA used was purchased from Coulter (Luton, UK). The assays were carried out on supernatants taken from infected cell cultures using the procedure described by the manufacturer. In each assay a positive control was included, together with a supernatant control taken from uninfected cells. The plates were read using the appropriate spectrophotometric detection system. Results of two separate assays are:

|  | Compound I | AZT | ddC |
| --- | --- | --- | --- |
| ID$_{50}$ | 0.1 $\mu$M | 0.003 $\mu$M | not determined |
| ID$_{50}$ | 6 $\mu$M | not determined | 0.01 $\mu$M |

ID$_{50}$ is defined as the dose of compound required to inhibit viral replication by 50 percent. The table above illustrates that Compound I exhibits anti-viral activity as does AZT. Approximately 0.1 $\mu$M and 6 $\mu$M of Compound I yields 50 percent inhibition of viral replication. 0.003 $\mu$M AZT provided 50 percent inhibition of viral replication in one test conducted. ddC provided 50 percent inhibition at a concentration of 0.01 μM in one test.

EXAMPLE 4

Formulations for Compound I

TABLET FORMULATION I

| Item | Ingredients | Mg/Tablet |
|---|---|---|
| 1 | Active ingredient | 20 mg* |
| 2 | Starch | 40 mg |
| 3 | Avicel | 80 mg |
| 4 | Lactose | 274 mg |
| 5 | Magnesium Stearate | 2 mg |
| | | 416 mg |

Method for Preparation:
1. Mix Items 3 and 4 in a suitable blender.
2. Add and mix the drug to the mixture from Step 1.
3. Add and mix Item 2 to the mixture from Step 2.
4. Add and mix Item 5 to the mixture from Step 3.
5. Compress the granulation on a suitable tablet press.

TABLET FORMULATION II

| Item | Ingredients | Mg/Tablet |
|---|---|---|
| 1 | Active Ingredient | 20 mg* |
| 2 | Lactose | 180 mg |
| 3 | Pregelatinized Starch | 15 mg |

Method for Preparation:
1. Mix Items 1, 2, 3, and 4 and granulate with water.
2. Dry the granulation at 45-50° C.
3. Pass the granulation through a suitable mill.
4. Add Items 5 and 6; mix.
5. Compress the granulation on a suitable tablet press.

*The amount of active ingredient i.e. Compound I or Compound I may be varied as required.

SOFT GELATIN CAPSULE FORMULATION

| Item | Ingredients | Mg/Tablet |
|---|---|---|
| 1 | Active ingredient | 20 mg* |
| 2 | Ethoxylated Fatty acids | 500 mg |
| 3 | PEG 4000 | 100 mg |
| 4 | Vegetable Oils q.s. to | 1.0 g |

Method for Preparation:
1. Add and mix drug with Items 2 and 4.
2. Add Item 3 to the material from Step 1 and mix.
3. Add vegetable oil to the required amount.
4. Fill into a suitable capsule.

ORAL LIQUID FORMULATION

| Item | Ingredients | Mg/Tablet |
|---|---|---|
| 1 | Active ingredient | 20.0 mg* |
| 2 | Methylparaben | 20.0 mg** |
| 3 | Sucrose | q.s. |
| 4 | Flavoring Agent | q.s. |
| 5 | Citrate Buffer | q.s.*** |
| 6 | Purified Water q.s. | 5.0 mL |

Method for Preparation:
1. Dissolve Items 2, 4, and 5 into purified water.
2. Add drug and dissolve into the solution from Step 1.
3. Add Item 3 and dissolve.
4. Add water to the required amount.
5. Fill the solution into a suitable container.

*The amount of active ingredient may be varied as required.

EXAMPLE 5

Formulations for Compound I and ddC

TABLET FORMULATION I

| Item | Ingredients | Mg/Tablet |
|---|---|---|
| 1 | Compound I | 20 mg* |
| 2 | ddC | 5 mg |
| 3 | Starch | 40 mg |
| 4 | Avicel | 80 mg |
| 5 | Lactose | 269 mg |
| 6 | Magnesium Stearate | 2 mg |

-continued

Formulations for Compound I and ddC 416 mg

Method for Preparation:
1. Mix Items 4 and 5 in a suitable blender.
2. Add and mix Item 1 and 2 to the mixture from Step 1.
3. Add and mix Item 3 to the mixture from Step 2.
4. Add and mix Item 6 to the mixture from Step 3.
5. Compress the granulation on a suitable tablet press.

TABLET FORMULATION II

| Item | Ingredients | Mg/Tablet |
|---|---|---|
| 1 | Compound I | 20 mg* |
| 2 | ddC | 5 mg** |
| 3 | Lactose | 175 mg |
| 4 | Pregelatinized Starch | 15 mg |
| 5 | Microcrystalline Cellulose | 72 mg |
| 6 | Modified Starch | 10 mg |
| 7 | Magnesium Stearate | 3 mg |
| | | 300 mg |

Method for Preparation:
1. Mix Items 1, 2, 3, and 4 then granulate with water.
2. Dry the granulation at 45-50° C.
3. Pass the granulation through a suitable mill.
4. Add Items 6 and 7; mix.
5. Compress the granulation on a suitable tablet press.

SOFT GELATIN CAPSULE FORMULATION

| Item | Ingredients | Mg/Tablet |
|---|---|---|
| 1 | Compound I | 20 mg* |
| 2 | ddC | 5 mg |
| 3 | Ethoxylated Fatty acids | 500 mg |
| 4 | PEG 4000 | 100 mg |
| 5 | Vegetable Oils q.s. to | 1.0 g |

Method for Preparation:
1. Combine and mix Items 1, 2, 3, and 5.
2. Add Item 4 to the material from Step 1 and mix.
3. Add vegetable oil to the required amount.
4. Fill into a suitable capsule.

ORAL LIQUID FORMULATION

| Item | Ingredients | Mg/Tablet |
|---|---|---|
| 1 | Compound I | 4.0 mg* |
| 2 | ddC | 1.0 mg** |
| 3 | Methylparaben | 2.0 mg |
| 4 | Propylparaben | 0.2 mg |
| 5 | Sucrose | 100.0 q.s. |
| 6 | Flavoring Agent | q.s. |
| 7 | Citrate Buffer | 5.0 mg |
| 8 | Purified Water q.s. | 1.0 mL |

Method for Preparation:
1. Dissolve Items 3, 4, 6, and 7 into purified water.
2. Add Items 1 and 2, and dissolve into the solution from Step 1.
3. Add Item 5 and dissolve.
4. Add water to the required amount.
5. Fill the solution into a suitable container.

PARENTERAL FORMULATION

| Item | Ingredients | Mg/Tablet |
|---|---|---|
| 1 | Compound I | 20.0 mg* |
| 2 | ddC | 5.0 mg |
| 3 | Propylene Glycol** | 20.0 mg |
| 4 | Emulphor | 2.0 mg |
| 5 | Water for Injection q.s | 1.0 mg |

Method for Preparation:
1. Dissolve Items 2 and 3 in water for injection.
2. Add and dissolve the drug in the solution from Step 1.
3. Adjust the pH using dilute sodium hydroxide or hydrochloric acid.
NOTE: Buffers such as citrate, acetate, or phosphate may be incorporated for adequate stabilization.
4. Add water for injection to the required amount.
5. Fill the solution into a suitable contained.

*The amount of Compound I may be varied as required.
**The amount of ddC may be varied as required.
***Solvents or solubilizers such as polyethylene glycols, alcohol, dimethylacetamide, glycerine, povidone, lecithin, sorbitan monooleate and trioleate, polysorbate 20 or 80 may be used in combination or alone to achieve the adequate solubility and stabilization.

I claim:

1. A method for treating a patient infected with a retrovirus comprising administering to the patient an anti-virally effective amount of a compound selected from the group consisting of a compound of the formula:

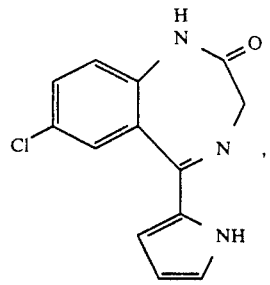

its pharmaceutically acceptable salts and mixtures thereof.

2. The method of claim 1 wherein the retrovirus is HIV.

3. The method of claim 2 wherein the anti-virally effective amount is 0.1–10 mg/kg body weight per day in one or more doses.

4. The method of claim 3 wherein the anti-virally effective amount is 1–3 mg/kg body weight given one to two times per day.

5. The method of claim 1 wherein the administration of the anti-virally effective amount results in a patient blood level of 0.05 to 10 mM.

6. The method of claim 5 wherein the administration of the anti-virally effective amount results in a patient blood level of 0.1 to 5 mM.

* * * * *

UNITED STATES PATENT AND TRADEMARK OFFICE
CERTIFICATE OF CORRECTION

PATENT NO. : 5,041,438

DATED : August 20, 1991

INVENTOR(S) : Ming-Chu Hsu

It is certified that error appears in the above-identified patent and that said Letters Patent is hereby corrected as shown below:

COLUMN 10

In claim 5 last line, replace "mM" with --$\mu$M--.

In claim 6 last line, replace "mM" with --$\mu$M--.

Signed and Sealed this

Twenty-third Day of February, 1993

Attest:

STEPHEN G. KUNIN

Attesting Officer      Acting Commissioner of Patents and Trademarks